US005811256A

United States Patent [19]
Bryant

[11] Patent Number: 5,811,256
[45] Date of Patent: Sep. 22, 1998

[54] METHOD FOR MEASURING SENSORY IRRITATION IN VITRO

[75] Inventor: Bruce P. Bryant, Elkins Park, Pa.

[73] Assignee: Monell Chemical Senses Center, Philadelphia, Pa.

[21] Appl. No.: 541,641

[22] Filed: Oct. 10, 1995

[51] Int. Cl.$^6$ .......................... C12Q 1/02; G01N 33/53; C12M 3/00; C12C 1/00
[52] U.S. Cl. ............................ 435/29; 435/7.2; 435/7.21; 435/284.1; 435/287.1; 435/288.2; 435/304.2; 435/305.1; 435/305.2; 435/968; 435/975; 435/288.4
[58] Field of Search ............................. 435/29, 7.2, 7.21, 435/284, 287, 300, 968, 975, 284.1, 287.1, 288.2, 304.2, 305.1, 305.2, 288.4

[56] References Cited

U.S. PATENT DOCUMENTS 5,424,218  6/1995  Miljanich et al. ...................... 436/503

OTHER PUBLICATIONS

Winter et al (Abstract), Brain Research, vol. 520(1–2), 1990, p. 131, month not available.
Donnelly, D.F. et al., "Hypoxia Decreases Intracellular Calcium in Adult Rat Carotid Body Glomus Cells", *Journal of neurophysiology*, Jun. 1992, 67:1543–1551.
O'Brien, Richard J. et al., "Isolation of Embryonic Chick Motoneurons and Their Survival in vitro", *The Journal of Neuroscience*, Nov. 1986, 6(11):3265–3274.
Akerman, K. and Gronblad, "Intracellular Free [Ca$^{2+}$] and [Na$^+$]in Response to Capsaicin in Cultured Dorsal Root Ganglion Cells", *Neuroscience Letters* 1992, 147, 13–15.
Api, Ann Marie, "Fragrances and the Skin Animal Alternatives", *Proceedings from the Sixth International Information Exchange*, Research Institute for Fragrance Materials, Inc., pp. 127–137, Nov. 19 & 20, 1992.

Belmonte, C. et al., "Excitation by Irritant Chemical Substances of Sensory Afferent Units in the Cat's Cornea", *J. of Physiology* 1991, 437, 709–725.
Bevan, S. and Szolcsanyi, "Sensory Neuron–Specific Actions of Capsaicin: Mechanisms and Applications", *TiPS* 1990, 11, 330–333.
Bowie, D. et al., "Subpopulations of Neonatal Rat Sensory Neurons Express Functional Neurotransmitter Receptors Which Elevate Intracellular Calcium", *Neuroscience* 1994, 58(1), 141–149.
Braa, S. and Triglia, "Predicting Ocular Irritation Using 3–Dimensional Human Fibroblast Cultures", *Cosmetics & toiletries* Dec., 1991, 106, 55–60.
Bryant, B. and Moore, "Factors Affecting the Sensitivity of the Lingual Trigeminal Nerve to Acids", *Am. J. Physiol.* 1995, 268, 58–65.
Church, M.K. et al., "Immunopharmacology of Mast Cells", in Pharmacology of the Skin I, Greaves, M. and Shuster, Eds., Springer–Verlag, Berlin, 1989, pp. 129–130.
Cohen, C. et al., "Episkin: An in Vitro Model for the Evaluation of Phototoxicity and Sunscreen Photoprotective Properties", *Toxic. in Vitro* 1994, 8(4), 669–671.
Dray, A. and Perkins, "Bradykinin and Inflammatory Pain", *Trends in Neuroscience* 1993, 16(3), 99–104.

(List continued on next page.)

Primary Examiner—Louise Leary
Attorney, Agent, or Firm—Woodcock Washburn Kurtz Mackiewicz & Norris LLP

[57] ABSTRACT

Methods for ascertaining the sensory irritation of chemicals in vitro are described. The methods include the cultivation of neuronal cells alone, with target tissue cells, and with target tissue cells and mast cells; the introduction of a chemical to be tested; and the measuring of neuronal response in the form of ion uptake or change in membrane potential. A co-culture system of neuronal and target tissue cells for performing said methods is also described.

29 Claims, 6 Drawing Sheets

OTHER PUBLICATIONS

Forbes, D. et al., "Co–Culture of Rat Trigeminal Ganglion Neurons and Corneal Epithelium", *Current Eye Research* 1987, 6(3), 507–514.

Garcia–Hirschfeld, J. et al., "Intracellular Free Calcium Responses to Protons and Capsaicin in Cultured Trigeminal Neurons", *Neuroscience* 1995, 67(1), 235–243.

Higgins, D. et al., "Tissue Culture of Mammalian Autonomic Neurons," in Culturing Nerve Cells, Banker, G. and Goslin, Eds., Massachusetts Institute of Technology, 1992.

Komai, M. and Bryant, "Acetazolamide Specifically Inhibits Lingual Trigeminal Nerve Responses to Carbon Dioxide", *Brain Research* 1993, 612, 122–129.

Lindahl, O., "Experimental Skin Pain Induced by Injection of Water–Soluble Substances in Humans", *ACTA Physiologica Scandinavica* 1961, 51 Supp. 179, 1–78, 87–89.

Liu, L. and Simon, "A Rapid Capsaicin–Activated Current in Rat Trigeminal Ganglion Neurons", *PNAS USA* 1994, 91, 738–741.

Montana, V. et al., "Dual–Wavelength Ratiometric Fluorescence Measurements of Membrane Potential", *Biochemistry* 1989, 28, 4536–4539.

Muller–Decker, K. et al., "Keratinocyte–Derived Proinflammatory Key Mediators and Cell Viability as in Vitro Parameters of Irritancy: A Possible Alternative to the Draize Skin Irritation Test", *Toxicology and Applied Pharmaclolgy* 1994, 127, 99–108.

Nagy, I. et al., "Cobalt Uptake Enables Identification of Capsaicin–and Bradykinin–Sensitive Subpopulations of Rat Dorsal Root Ganglion Cells in Vitro", *Neuroscience* 1993, 56(1), 241–246.

Nielsen, g. and Hansen, "Sensory Irritation of the Upper Respiratory Tract",*Pharmacology & Toxicology* 1993, 72, 32–35.

Ollmar, S. and Emtestam, "Electrical Impedance Applied to Non–Invasive Detection of Irritation in Skin", *Contact Dermatitis* 1992, 27, 37–42.

Ponec, M. and Kempenaar, "Use of Human Skin Recombinants as an in Vitro Model for Testing the Irritation Potential of Cutaneous Irritants", *Skin Pharmacol.* 1995, 8, 49–59.

Rang, H.P. et al., "Chemical Activation of Nociceptive Peripheral Neurones", *British Medical Bulletin* 47(3), 534–548.

Restrepo, D. et al., "Imaging of Intracellular Calcium in Chemosensory Receptor Cells", in Experimental Cell Biology of Taste and Olfaction, Current Techniques and Protocols, CRC Press, Inc., 1995, pp. 387–398.

Roguet, F. et al., "Use of in Vitro Skin Recombinants to Evaluate Cutaneous Toxicity: A Preliminary Study", *J. Toxicol.–Cut.& Ocular Toxicol.* 1992, 11(4), 305–315.

Roguet, R. et al., "Episkin, a Reconstituted Human Epidermis for Assessing in Vitro the Irritancy of Topically Applied Compounds", *Toxicology in Vitro* 1994, 8(2), 283–291.

Steen, K. et al., "Protons Selectively Induce Lasting Excitation and Sensitization to Mechanical Stimulation of Nociceptors in Rat Skin, in vitro", *The J. of Neuroscience* 1992, 12(1), 86–95.

Yang, W. and Acosta, "Cytotoxicity Potential of Surfactant Mixtures Evaluated by Primary Cultures of Rabbit Corneal Epithelial Cells", *Toxicology Letters* 1994, 70, 309–318.

Zhang, X.–S. and Bryant, "A Subpopulation of Cultured Neonatal Rat Trigeminal Neurons Expresses Both CGRP and Sensitivity to Capsaicin", Association for Chemoreception Sciences meeting Abstracts, Sarasota, Florida, Apr. 19–23, 1995.

Hotchkiss, S., "Percutaneous Absorption, Metabolism & Parmacokinetics of Fragrance Chemicals", in Proceedings from the Sixth Int. Information Exchange of the Research Institute for Fragrance materials, Inc., Nov. 19 & 20, 1992, Princeton, New Jersey, p. 101.

METHOD FOR MEASURING SENSORY IRRITATION IN VITRO

REFERENCE TO GOVERNMENT RIGHTS

This invention was made, in part, with Government support. The Government may have certain rights in this invention.

FIELD OF THE INVENTION

This invention relates to methods for measuring the sensory irritation of chemicals in vitro.

Background of the Invention

Previously, laboratory animals were used to assess the safety, and possible risk to humans, of both raw materials and finished products used in cosmetics, perfumes, personal care products, household products, petrochemical products, and the like. Specifically, the Draize tests in the rabbit were used for evaluating skin and ocular irritation. However, the use of animals for such testing has fallen into much disfavor, not only for humane reasons, but also due to questions of their predictive value. Accordingly, the search for alternative testing means has ensued. In the course of this search, various in vitro testing methods have been developed utilizing cell-based and model-skin systems.

One example of an in vitro model which has been developed is Skin$^2$, manufactured by Advanced Tissue Sciences. Skin$^2$ is a human cell culture derived from neonatal foreskins. A comparison of in vitro results obtained with Skin$^2$ with results obtained using the traditional Draize rabbit skin testing is reported in Ann Marie Api, "Fragrances and the Skin Animal Alternatives," *Proceedings from the Sixth International Information Exchange,* Research Institute for Fragrance Materials, Inc., pp. 127–137, Nov. 19 & 20, 1992. Three endpoints were tested in the in vitro method, all of which measure cytotoxicity through cell injury or cell death. The in vitro results did not correlate well with the in vivo results. It was concluded that the in vitro model's strength was not in distinguishing irritants from non-irritants, or as a replacement for the in vivo test, but more as a means for elucidating the mechanisms involved in inflammation. Further, the authors observed that most fragrance materials are not necrotic.

In another study, the comparison between the Skin$^2$ system and the Draize rabbit unwashed eye test seemed to be more favorable. The endpoints used, however, still measured cytotoxicity. The authors observed that multiple endpoints can become a necessity due to the incompatibility of some endpoints with high concentrations of certain chemicals. Braa et al., *Cosmetics & Toiletries,* 106:55–60, December, 1991.

Cytoxicity of chemicals has also been measured in primary cultures of rabbit corneal epithelial cells. See, for example, Yang et al., *Toxicology Letters,* 70:309–318, 1994, herein incorporated by reference. Comparison with the Draize rabbit eye test revealed substantial agreement for the chemicals tested. It was, nonetheless, concluded that a battery of cytotoxicity assays is needed in an in vitro system to quantitatively measure cell injury.

Others have measured irritation as the release of proinflammatory mediators by monolayers of human keratinocytes in culture. Muller-Decker et al., *Toxicology and Applied Pharmacology,* 127:99–108, 1994. Graded release of proinflammatory mediators in response to graded irritant potential was shown. Nonetheless, it was concluded that the measurement of multiple mediator endpoints is necessary.

Still others have measured cytotoxicity, release of proinflammatory mediators, morphology, and barrier function in a reconstituted human epidermis: Episkin—Roguet et al., *Toxicology In Vitro,* 8(2):283–291, 1994; and Living Skin Equivalent (LSE)—Organogenesis, Cambridge, Mass. and Ponec et al., *Skin Pharmacol.,* 8:49–59, 1995. However, since neither LSE™, Skin$^2$, nor Episkin contain sensory nerve or mast cells, certain sensory or inflammatory phenomena cannot be measured.

Most of the foregoing procedures utilized measurements of cytotoxicity or of released products of inflammation. However, as described in Nielsen et al., *Pharmacology & Toxicology,* 72:32–35, 1993, sensory irritation is distinct from cytotoxicity. Sensory irritation includes more subtle sensations such as cool, warm, itching, piquancy, pungency, stinging and tickling. It can rise to the level of painful and/or burning sensations, inducing tears or nasal and salivary secretions via neural excitation. Endpoints measuring cytotoxicity and/or products of inflammation alone will not satisfactorily gauge sensory irritation.

Sensory irritation involves neuronal participation. Certain neurons are nociceptive, i.e., capable of transmitting pain. Some "nociceptors", i.e., those that are polymodal, can be stimulated in a variety of ways including indirectly through action of transmitter substances. Bevan et al., *TiPS,* 11:330–333, August, 1990, report the effect of capsaicin, the ingredient in peppers which elicits the burning pain sensation, on such neurons in culture. Neonatal rat dorsal root ganglion neurons in culture exhibited an influx of $Ca^{++}$ upon stimulation with capsaicin. The uptake of $Ca^{++}$ was measured using $^{45}Ca^{++}$. The sensitivity to capsaicin is reported therein to be regulated by nerve growth factor (NGF).

Bowie et al., *Neuroscience,* 58(1):141–149, 1994, describe the attempted identification of subpopulations of neonatal rat sensory neurons which possess functional neurotransmitter receptors which elevate free concentration of intracellular calcium. Subpopulations were distinguished on the basis of cell diameter. A variety of receptor agonists were tested including capsaicin, bradykinin, ATP, adenosine, and substance P. It is reported that, with the exception of ATP, the rise in intracellular calcium was restricted to small (<17 $\mu$M) and intermediate (17–25 $\mu$M) cells. The percentage of cells responding for bradykinin is reported in Table 3. Eight other receptor agonists tested failed to elevate intracellular calcium and the authors opined that it might be due to a developmental effect.

Previous studies involving cultured neurons utilized single cell-type cultures, and focused upon elucidating mechanisms of response. None, however, suggested the use of cultured neurons for measuring sensory irritation. Forbes et al., *Current Eye Research,* 6(3):507–514, 1987, developed a co-culture system of a target tissue—the corneal epithelium—and trigeminal ganglion neurons. One main focus of the report was the visual monitoring of the cultures using phase-contrast microscopy. Accordingly, the co-culture was set-up to facilitate such visual monitoring. Both cell types were cultured on the same contiguous bed of collagen, in the same plane. The neurons were separated from the epithelial cells by a glass cloning cylinder having one end covered by a fine ribbon of high vacuum silicone grease. The neurons were cultured until neuritic processes penetrated under the grease seal and extended into the outer chamber. Small pieces of corneal epithelium were plated in the same plane as the neuritic processes on the same collagen bed. The authors assert that, in such a culture, each cell type can be independently treated, and that, if the nerve cell bodies in the inner chamber are affected by treatment of the corneal epithelium, it might be concluded that some type of interaction has occurred and that the neurites have transported some message to their cell bodies. However, in such a culture, the neurites will be directly subject to the same treatment as the corneal epithelium as they are exposed in the same chamber, in the same plane to the medium. Thus, it does not appear that each cell type can be independently treated. The testing of drug treatments, growth factors, infectious agents, etc. is suggested, but there is no suggestion of measuring sensory irritation.

An in vitro method for testing the sensory irritation of chemicals is still needed.

SUMMARY OF THE INVENTION

The present invention improves upon current methods for measuring the irritancy of chemicals, in particular, the sensory irritation of such chemicals. Sensory irritation is differentiated from chemical irritation in general; it includes pain and less intense forms of irritation which can be induced by chemicals in a manner that does not necessarily cause cellular damage or loss of cellular viability. Sensory irritation is mediated by the activation of certain nerves that are present throughout many tissues and organs of the body.

In one aspect, the present invention is directed to a method for assessing the sensory irritation of chemicals in vitro. Afferent neonatal neurons are exposed to the chemicals to be tested in culture, and select responses are compared with those of controls.

In another aspect, the present invention is directed to a method for assessing the sensory irritation of chemicals in vitro using a co-culture of afferent neonatal neurons and cells from a representative target tissue. The neuronal and target tissue cells are cultured in different chambers separated by a material which allows the neurons to penetrate and innervate the cultured epithelium. The target tissue cells are exposed to the chemicals in culture, and neuronal responses are compared with those of controls.

In yet another aspect, the invention relates to a method for assessing hypersensitization by chemicals involving the exposure of the neuronal or target tissue cells to a first chemical or photic stimulus followed by exposure to a second chemical or photic stimulus.

In a further aspect, the present invention relates to a kit for assessing the sensory irritation of chemicals in vitro.

In yet a further aspect, the present invention relates to a co-culture system for testing the sensory irritation of chemicals. The system includes neuronal cells and target tissue cells.

DETAILED DESCRIPTION OF THE INVENTION

Figure 1:
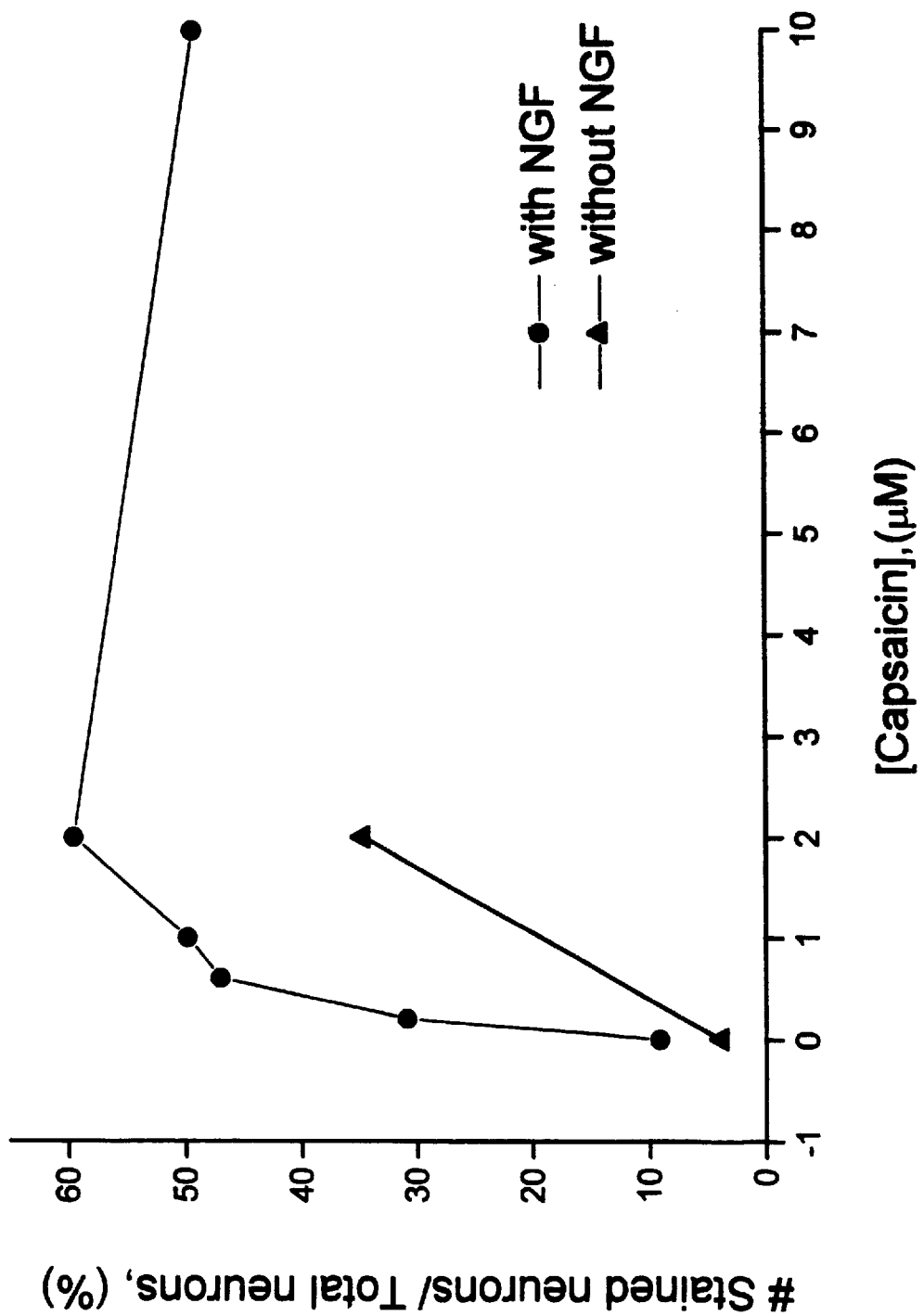
FIG. 1 depicts the relation of cobalt ion uptake by neurons to capsaicin (sensory irritant) concentration, as measured using silver enhancement staining of cobalt sulfide.

The invention described below improves upon current techniques of assessing irritation by including the measurement of neural activation, the necessary condition for signaling pain and other types of sensory irritation, including itch and other paresthesias.

In a preferred embodiment, the system is comprised of an in vitro co-culture model of a target tissue that normally receives sensory innervation, and afferent neuronal cells. The method includes several alternative techniques for measuring neural activation in vitro. However, afferent neuronal cells alone can also be utilized in the event the particular stimulus may act directly on the neurons.

The invention is based on the measurement of neuronal activation by irritants. Sensory irritants, for example, capsaicin, cause neuronal activation by opening ion channels in the membranes of polymodal nociceptors and warm sensitive neurons Bevan et al., supra. Other irritants (e.g. the carbon dioxide in carbonated beverages, and food-derived short chain fatty acids) also stimulate other classes of somatosensory neurons. Komai, et al., *Brain Research* 612:122–129, 1993. Bryant, et al., *Am. J. Physiol.* 268:58–65, 1995).

Psychophysical studies demonstrate that a subcutaneous pH of 6.2 is sufficient to cause pain in humans and that the perception of pain increases with increasing hydrogen ion concentration Lindahl, *ACTA Physiologica Scandinavica*, 51(179):1–89, 1961. Single-unit recordings from mammalian nerves show that protons activate a subpopulation of afferents innervating skin and cornea Steen et al., *The Journal of Neuroscience*, 12(1):86–95, 1992; Belmonte et al., *Journal of Physiology*, 437: 709–725, 1991. In single trigeminal ganglion (TG) neurons, inward currents activated by protons at pH 6 share similarities with capsaicin (CAP) -activated inward currents Liu et al., *Proc. Natl. Acad. Sci., USA*, 91: 738–741, 1994.

As a result of the opening of the ion channels in response to the sensory stimulus, there is an influx of cations, such as $Ca^{++}$. The resultant influx of cations can be measured several ways. With the substitution of cobalt ions for calcium in the culture medium, activation of the ion channels can be measured by the precipitation of intracellular cobalt sulfide from ionic cobalt (as $CoCl_2$, 5 $\mu$M, incubation for about 5–10 minutes) that has entered the cell. The precipitate can then be enhanced by a silver precipitation enhancement technique. Nagy, et al., *Neuroscience*, 56(1):241–246, 1993, incorporated herein by reference.

Alternatively, intracellular calcium can be measured directly using fluorescence microscopical techniques. Briefly, a fluorescent calcium-indicating dye (i.e., FURA-2) is introduced into cells, specifically, as the cell-permeant acetoxymethylester (FURA-2AM, 2–10 $\mu$M, for about 30–60 minutes). Intracellular esterases produce the free acid which, upon binding free calcium ions, changes its fluorescent properties in proportion to the concentration of free calcium ion present (typically ranging from 50–1000 nM).

Thus, the extent of cellular activation is indicated by the change in intracellular calcium. Restrepo et al., *CRC Press, Inc.*, pp. 387–398, 1995, incorporated herein by reference.

In yet another alternative, changes in membrane potential, can be analyzed as a result of exposure to the test chemical using a voltage sensitive fluorescent dye (i.e., Di-4-ANEPPS) Montana, et al., *Biochemistry* 28: 4536–4539, 1989, incorporated herein by reference, in place of a calcium indicating dye. Incubations with voltage sensitive dyes will generally be from about 5 to about 30 minutes.

The system of the invention can be composed of epithelial (i.e., keratinocytes and fibroblasts), endothelial, visceral organ, and muscle cells, isolated from the relevant target tissues including, but not limited to, the skin, eyes, throat, stomach, trachea, lungs, nose, mouth, bladder, liver, etc. Model skin systems are currently available (i.e., Clonetics Corp.; Advanced Tissue Sciences; Roguet et al., 1994, supra) which can be modified to comport with the system according to the invention. One necessary modification is the inclusion of afferent neuronal cells to provide a model of innervated epithelium, or other organ or tissue. A further modification can be the inclusion of mast cells, the elements of cutaneous tissue which, when provoked by the appropriate stimuli, release compounds such as histamine, and 5-hydroxytryptamine (serotonin), as well as other components of the cutaneous defensive reaction which are involved in the inflammatory response and associated pain.

Chemicals can, according to the invention, be simultaneously assessed for their ability to 1) directly cause pain or other forms of sensory irritation by stimulation of somatosensory neuronal endings; 2) cause pain or irritation by stimulation of release of endogenous irritating compounds from mast cells which subsequently activate nerve endings or compounds released from keratinocytes or fibroblasts (i.e. proinflammatory mediators such as arachidonic acid, PGE-2, etc.) which sensitize nociceptors; and 3) cause pain or irritation by damage to the epithelium or organ or tissue per se which would be sensed by nerve endings as the release of cell contents (i.e. ATP). Test chemicals are added for up to about 1 hour when target tissue cells are not included, and from about 1 minute to about 1 hour when target tissue, with or without mast cells, is included.

The neurons utilized according to the invention must be susceptible to stimulation at their dendrites. The sensory neurons can be isolated from trigeminal, dorsal root, or nodose ganglia.

The system and methods can be used as a screening tool to assess the sensory irritation potential of a variety of pharmaceuticals, oral care products, skin care products and cosmetics, gastrointestinal medicines, nasal medicines, as well as products that contact the eye, and products injected IV or IM. The system and methods can also be used to assess the irritancy of environmental contaminants on respiratory tissue—i.e., trachea and alveolar tissue. To assay compounds which would contact such targets, the appropriate testing system includes a co-culture of the corresponding epithelium, endothelium, or muscle tissue innervated in vitro by neurons obtained from the corresponding sensory ganglion. The system can further contain the appropriate density of mast cells if present in the native target tissue. The appropriate density of mast cells can be estimated from the literature (see, for example, Church, et al. *Pharmacology of the Skin I*, 1989, incorporated herein by reference), and optimized empirically.

Figure 5:
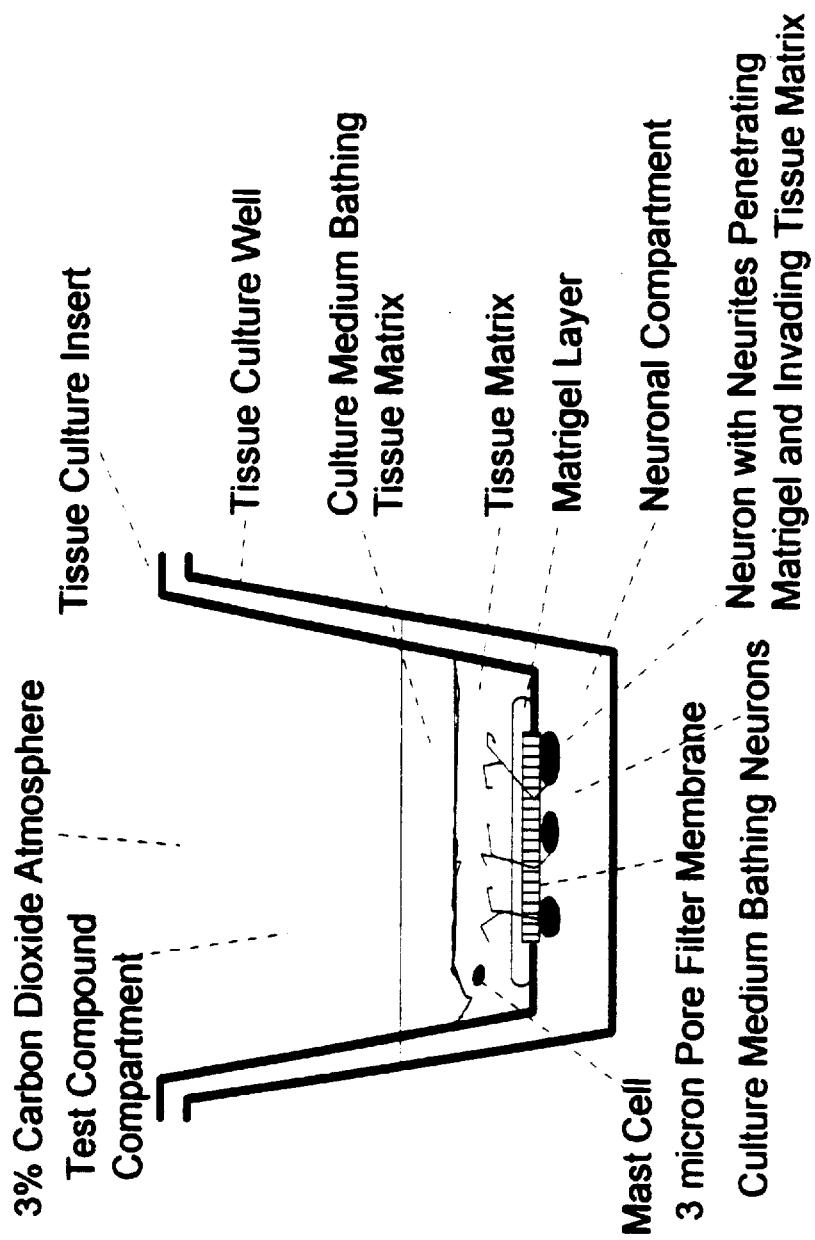
FIG. 5 depicts the co-culture system of the tissue matrix (epithelial and mast cells) and neuronal cells according to the invention.

FIG. 5 illustrates a co-culture system according to the invention. The culture of tissue cellular matrix—appropriately constituted combination of keratinocytes, fibroblasts, mast cells and other cellular elements—is on the interior of tissue culture inserts (Collaborative Biomedical Products). Sensory neurons are cultured on the exterior surface of the bottom of the insert and are bathed in the culture medium (DMEM/F12, 1:1) contained in the external well of the culture plate. The sensory dendrites of the neurons grow through the pores (approximately 3 $\mu$m in the membrane on the bottom of the insert and invade the tissue matrix. The test chemicals are added to the tissue matrix side of the insert. The fluid height in the external well is maintained at a level above the fluid height inside the insert so that the test chemicals are kept from passing to the outer chamber due to hydrostatic pressure. In this manner, the dendrites will be exposed only to test chemicals that have diffused through the tissue matrix and/or chemicals that are released by the tissue matrix in response to the test chemicals. Chemicals can also be added to either compartment to test for sensitization or inhibition of sensory irritation. Measurement of neural activation entails, for example, substitution of cobalt-containing solution for the culture medium in the exterior compartment. Alternatively, the insert and attached cells and neurons can be removed from the culture well and the changes in neuronal intracellular calcium or membrane potential can be quantitated using fluorescence microscopy.

The primary advantage of the invention is that it can assess the potential for pain and irritation in chemicals that are not in themselves toxic or damaging to tissue. The term "chemical", as used herein, includes compounds or mixtures of compounds or extracts of plant or animal tissue in liquid, aerosol, or gaseous form. This ability is not afforded by systems that measure cell damage or cell viability, nor systems that do not include neuronal cells. Only by measuring neuronal activation per se can sensory irritation be assessed.

In addition to measuring irritation of the intensity that would be considered painful, the invention can also indicate the potential for irritation at lower intensities, i.e. paraesthesias such as tingling, itching, or mild burning. This would be achieved by using the fluorescent techniques that measure reversible changes in neuronal intracellular calcium or membrane potential. Before applying test compounds to the system, individual cultured sensory neurons would be characterized and calibrated by application of ranges of concentrations of compounds known to induce itch (histamine) or warming (low concentrations of capsaicin), for instance as well as thermal stimuli. Further, because there are receptors present on some sensory neurons that are sensitive to certain cell contents that are released upon cell damage (i.e., ATP), the invention is also capable of monitoring sensory irritation that is a result of cell damage.

In both veterinary and human applications, where the assessment of pain and less intense forms of sensory irritation is difficult, the invention will greatly aid in predicting the potential for pain and/or irritation by providing a non-invasive means of measurement that would also simultaneously greatly reduce the number of animals or human subjects needed to evaluate such products. Further, this system requires many fewer animals as tissue donors, and these donors would be under anesthesia, therefore suffering less distress during the donation of tissue than with previous testing.

The sensitivity of the system is expected to be at least as great as the system of interacting neurons and the surrounding cellular matrix in an intact animal. In many of the applications mentioned above, a determining variable in regulating sensitivity is the presence of an intervening keratinized epithelium, which serves as an effective permeability barrier to potential sensory irritants; the greater the degree of keratinization, the less sensitive the system will be. In the system according to the invention, the degree or presence of a keratinized layer(s) of cells can be controlled, thus regulating the access of irritants to the sensory dendrites.

The sensitivity of the system will also depend upon the presence of nerve growth factor (NGF), the concentration of which can be varied in the culture medium. The maintenance of sensitivity of cultured dorsal root ganglion neurons to capsaicin is dependent upon the presence of NGF (Bevan, et al., supra, p.3).

An additional factor affecting sensitivity is the density of mast cells present in the matrix for stimulated release of endogenous irritants. The density and sensitivity of mast cells can be modulated by controlling the culture conditions. For putative irritants that may act directly upon the dendrites of the sensory neurons and not require intervening secretion of agents from mast cells or other elements of the tissue matrix, the system can be configured to include only neurons. In this case, the test substance would directly contact the sensory neuron dendrites.

Additionally, the process of axon reflex, an important aspect of immediate and sustained pain in irritation and inflammatory situations, is included in this complex of neuronal and nonneuronal elements. Axon reflex refers to the efferent function of sensory endings whereby adequate peripheral stimulation causes peripheral release of substance P, calcitonin-gene-related peptide (CGRP), and other compounds involved in the inflammatory response. These compounds are active in causing mast cell discharge and in causing hypersensitization of peripheral nerve endings. Thus the presence of competent nerve endings in the epidermal, endodermal, or other types of tissue matrix provides a more complete in vitro model of pain, irritation, and inflammatory processes than tissue matrix assay systems without innervation.

Finally, the invention can be used to determine long term, sensitizing interactions between potential irritants, i.e., hypersensitization. To assess for hypersensitization, the system is first exposed to a priming or sensitizing stimulation in the absence of cobalt ions for a period of from about 0–2 days. Subsequently, the chemical to be tested is added in the presence of cobalt or Ca$^{++}$ ions (depending upon the method used to quantitate neuronal activation) for a period of from about 0–20 minutes. Hypersensitization can then be determined and quantified by comparison with a system that was not exposed to the first priming stimulus. For further validation, comparison with systems not receiving the second stimulus, or receiving neither stimulus, can be made. This application of the invention applies not only to interactions between chemicals, but also to examining chemical sensitization to thermal and photic (i.e. UV radiation) stimuli as a result of chemical stimuli, as well as the reverse processes of sensitization to chemical stimuli by thermal or photic stimuli.

The following examples are meant to illustrate the invention and not to limit it in any way. Those skilled in the art will recognize that modifications can be made which are within the spirit and scope of the invention as set forth in the appended claims.

EXAMPLE 1

Neurons from neonatal (2–4 day old) trigeminal ganglia (TG) of the rat were prepared following the general method of Higgins et al., *Massachusetts Institute of Technology*, 1992, incorporated herein by reference, and cultured in the presence of nerve growth factor (NGF) (0.5 μg/ml) in DMEM/F12(1:1) medium. Cells were cultured at an initial density of $10^5$ cells/cm$^2$ on glass coverslips in 12-well plates. After about 2–10 days in culture, the cells were characterized by assaying for the presence of neuron specific enolase (NSE, a form of the enzyme enolase that is found only in neurons), the neuropeptides calcitonin gene-related peptide (CGRP) and substance P, and sensitivity to capsaicin. Cells of 17–40 μm diameter and typical neuronal morphology were found to contain NSE. Capsaicin sensitivity was determined using a cobalt precipitation technique. Nagy, et al., supra. Cells on coverslips were exposed to capsaicin in a medium containing cobalt ions at a concentration of 0–10 μM for 5 minutes. (NH$_4$)$_2$S was added after at a concentration of 0.12% (v/v) for 5 minutes. After fixation of the cells in 4% paraformaldehyde/phosphate buffered saline, the resultant precipitate was enhanced by adding AgNO$_3$ at 0.1% (w/v), 292 mM sucrose, 15.5 mM hydroquinone and 42 mM citric acid and incubating at 50° C. for 40 minutes.

Figure 3:
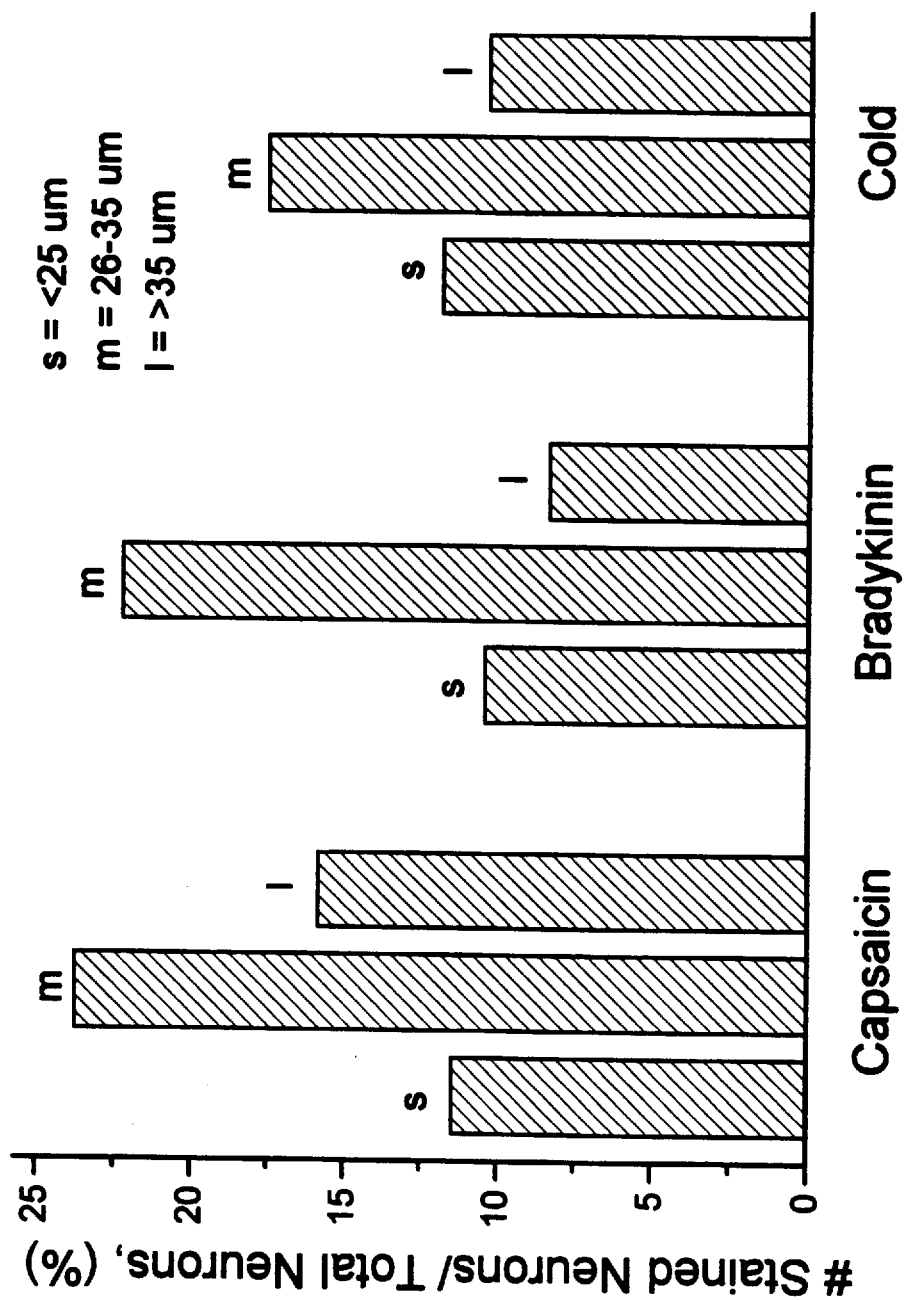
FIG. 3 depicts the relationship between response and the size of the neuron, as measured using cobalt ion/silver enhancement staining.

Neurons exhibited capsaicin sensitivity in a dose dependent manner; the percentage of neurons that specifically took up cobalt in the presence of capsaicin increased to 60% as the concentration of capsaicin increased from 0 to 2 μM. This is depicted in FIG. 1. Non-neuronal cells did not exhibit staining. FIG. 3 indicates that capsaicin sensitivity was observed throughout the range of 17–>36 μm diameter neurons. Using immunofluorescence techniques, CGRP was detected in 5.2% of neurons in culture. Substance P immunoreactivity was weak in 2–4 day old cultured cells and not detectable in cells that had been exposed to the conditions of the cobalt uptake assay for capsaicin sensitivity.

EXAMPLE 2

In the cultured neonatal rat neurons of Example 1, a subpopulation of CAP-sensitive neurons expressed CGRP using the cobalt uptake assay and immunocytochemical technique. However, proton-sensitive neurons were not detected. This suggested that CAP and proton sensitivity may be mediated by different mechanisms or that the cobalt precipitation technique is not appropriate for acidic conditions.

Figure 4:
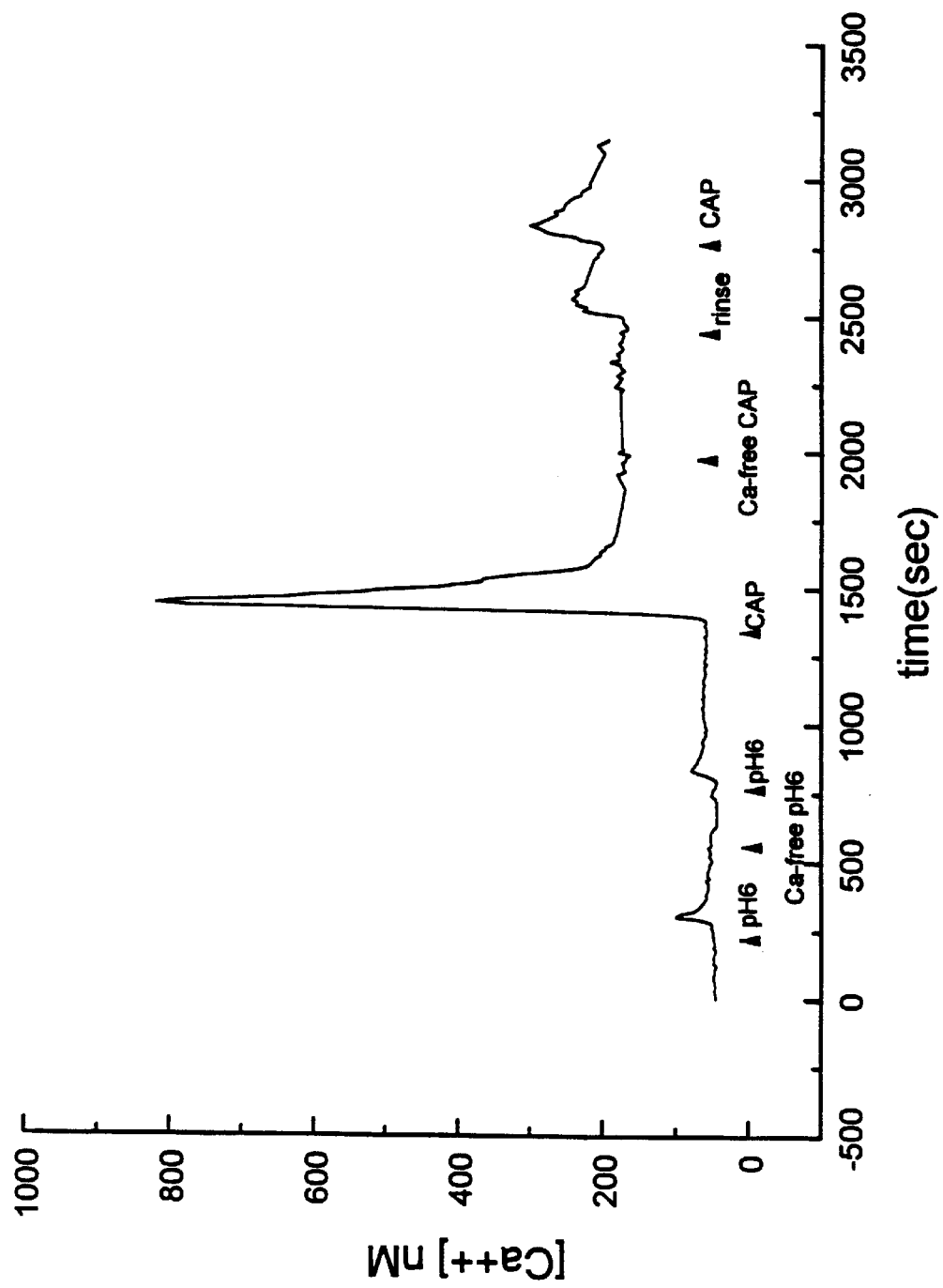
FIG. 4 depicts the $Ca^{++}$ uptake by neurons in response to low pH and capsaicin, as measured by fluorescence ratio imaging of FURA-2 loaded neurons.

Using the Ca$^{2+}$-sensitive indicator FURA-2, Restrepo et al., *CRC Press, Inc.*, pp. 387–398, 1995, incorporated herein by reference to measure intracellular [Ca$^{2+}$] in TG neurons, it was found that 0.25 μM CAP (30 seconds) elevated the concentration of intracellular free Ca$^{2+}$ in 62% of cultured neonatal TG neurons. A typical response is depicted in FIG. 4. The neurons were loaded with FURA-2 (5 μM, 30–60 minutes) by incubating in FURA-2-AM-containing medium. Culture medium containing 2 μM Ca$^{2+}$ was added. Intraneural calcium concentration was calculated from the ratio of fluorescence intensity values obtained from illumination at 340 to 360 nm.

It was also found that 20% of the neurons responded only to low pH (i.e., ≦5.0, 30 seconds). Protons (pH<6.6) caused either a decrease or increase of intracellular [Ca$^{2+}$] in different neurons. The percentage of CAP-sensitive neurons which responded to protons with a decrease in intracellular [Ca$^{2+}$] was concentration dependent in the range of pH 6.5 to pH 5. All neurons which responded to protons with an increase in intracellular [Ca$^{2+}$] were also sensitive to 0.25 μM CAP. The percentage of neurons which responded to protons with an increase in intracellular [Ca$^{2+}$] was constant across the range of pH 6.5 to pH 5. While this heterogeneity may reflect acid-sensitive processes on the cell body, it may also reflect the presence of an additional proton sensitive transduction mechanism that is independent from CAP sensitivity, yet important to process of sensory irritation by acid. The extracellular $Ca^{2+}$ concentration was 2 $\mu$M and FURA-2-AM was added at a concentration of 5 $\mu$M.

EXAMPLE 3

The response of the neuronal cells to a variety noxious stimulants was tested. The culture conditions were as in Example 1 above. The following stimulants were tested at levels known to be noxious or painful: capsaicin (2 $\mu$M), bradykinin (1 $\mu$M), and cold (4°–8° C.). As described above, capsaicin induces sensations of heat and pain. Bradykinin is a proinflammatory mediator which also induces pain. Dray et al., *Trends in Neuroscience*, 16(3):99–104, 1993, incorporated herein by reference. Neurons were exposed to test chemicals or cold for 5 minutes.

Figure 2:
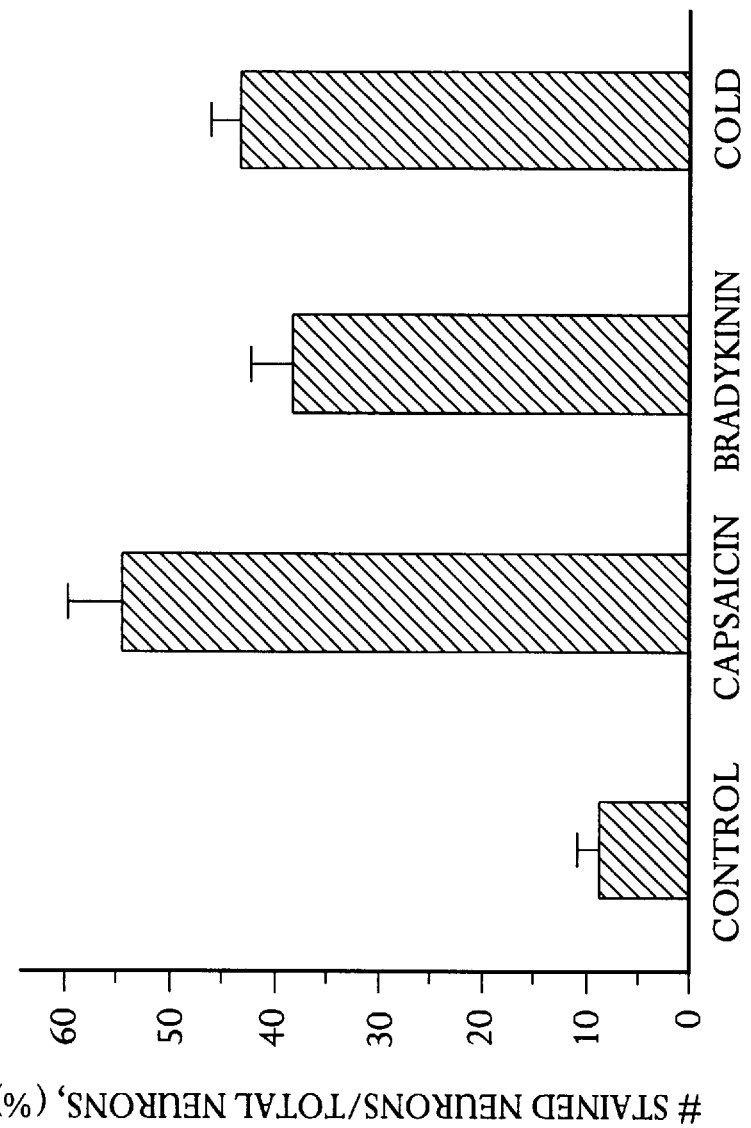
FIG. 2 depicts the cobalt ion uptake by neurons in response to capsaicin (2 $\mu$M), bradykinin (1 $\mu$M), and cold (4°–8° C.) stimuli, as measured using silver enhancement staining of cobalt sulfide.

The results are depicted in FIGS. 2 and 3. As can be seen from FIG. 2, for all three stimulants, the percentage of stained neurons was at least approximately four times that of the controls. Thus, the system detects a variety of types of noxious sensory stimulation. FIG. 3 depicts the response as a function of the size of the neuronal body. Cells having a diameter of 17–25 $\mu$m were designated as small; medium cells had a diameter of 26–35; and large cells had a diameter of >36 $\mu$m. As is evident from FIG. 3, although the small to medium cells are considered the polymodal subpopulation of nociceptors, even the large cells were responsive to noxious stimuli in culture. Rang, et al., *British Medical Bulletin*, 47(3): 534–548, incorporated herein by reference.

EXAMPLE 4

Figure 6:
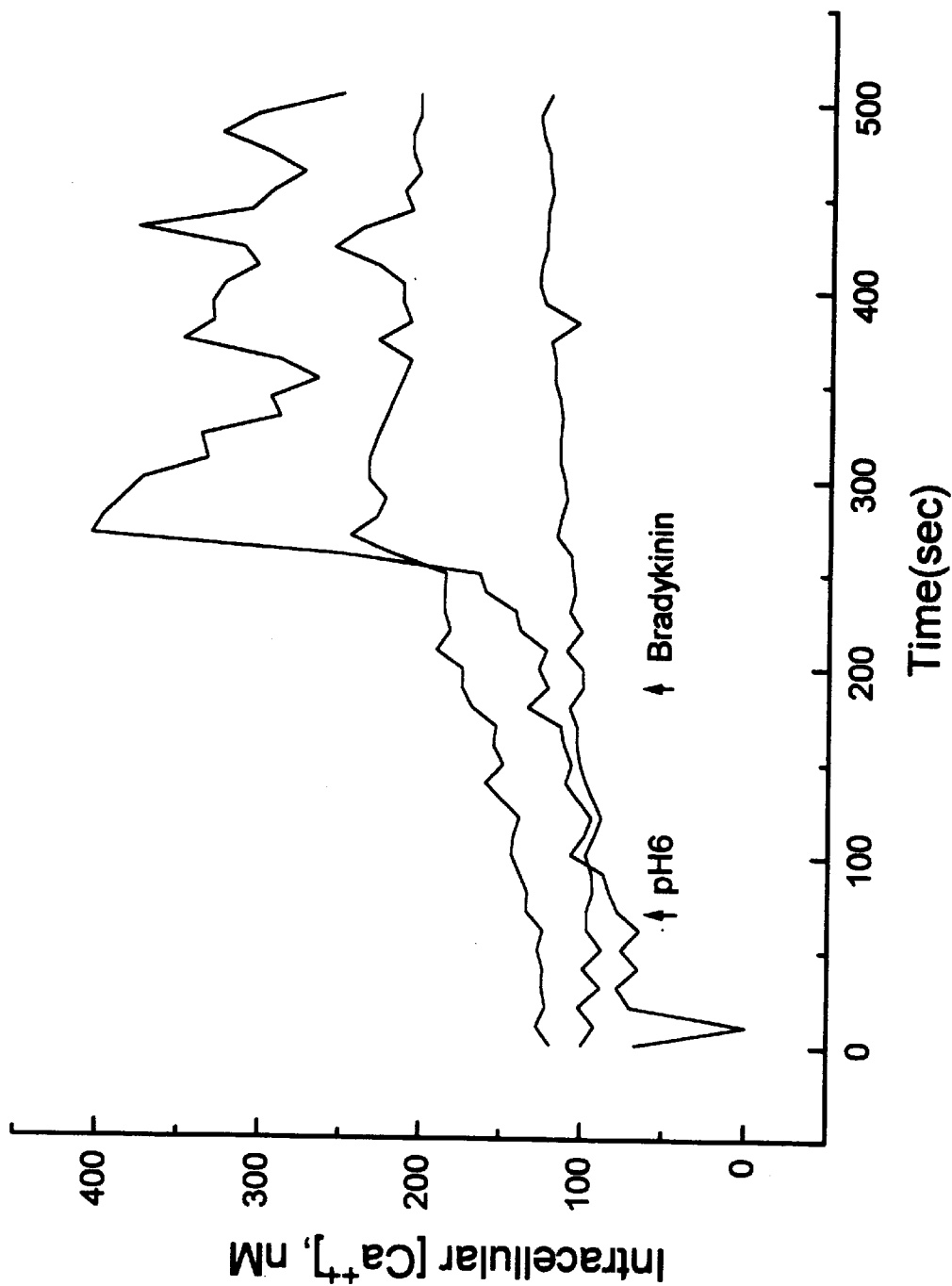
FIG. 6 depicts calcium uptake by the cell bodies of neurons, the neurites of which were exposed to bradykinin (1 micromolar) and pH 6, as measured using FURA-2. Neurons were cultured on one side of a tissue culture insert membrane. The neurites penetrated the pores of the membrane and invaded a layer of Matrigel that had been formed on the side opposite to the neural cell bodies. The cell bodies did not receive chemical stimulation.

The response of trigeminal neurons to selective stimulation of the neurites was tested in the following manner. Cells from neonatal trigeminal ganglia were cultured on one side of a 3 micron pore filter membrane. On the opposite side of the membrane, a 100–200 micron thick layer of Matrigel had been deposited prior to culture. By the end of 7 days in culture, neurites were observed by phase contrast microscopy to have penetrated the filter and invaded the layer of Matrigel. Changes in intracellular calcium in response to bradykinin (1 $\mu$M) and low pH (pH 6) were observed by placing the membrane with FURA-2 loaded neurons and neurites on a coverslip on an inverted epifluorescence microscope. The neuronal cell bodies were placed adjacent to the coverslip in calcium-containing culture medium. The edges of the membrane were sealed to the coverslip with petrolatum jelly. Selective stimulation of the neurites was obtained by application of a flow of stimulus to the neurite side of the membrane. Excess stimulus flow was removed continuously by vacuum. FIG. 6 depicts the responses to bradykinin and acidic pH (pH 6). Two neurons responded to bradykinin, one also responded slightly to pH 6, and one was unresponsive. The delay in response onset (arrow) represents the time it takes for the stimulus to arrive at the neurons from the stimulus switching device.

EXAMPLE 5

Epithelial cells isolated from, for example, rat tissue (i.e., tongue, skin, cornea, etc.) are inoculated at $10^5$ cells per cm$^2$ on the inside of a collagen-coated tissue culture insert. In a preferred embodiment, mast cells are included at the appropriate density for the tissue from which the epithelial cells are isolated. Similarly, a layer of Matrigel® (100–200 $\mu$m thick) may be deposited on the membrane surface before the epithelial cells are added, to aid in the initial growth of the epithelial cells and of the invading neurites. After 2–4 days the insert is inverted under sterile conditions and sensory ganglion cells (i.e., DRG cells) are inoculated at $10^5$ cells per cm$^2$ on the collagen coated membrane on the outer bottom of the insert. Once the DRG cells have adhered to the membrane, the insert is placed upright into a culture well (12 well culture plate) containing DMEM/F12 culture medium. The same culture medium is added to the interior of the insert. The culture is maintained until neurites have passed through the filter membrane and the epithelial cells are confluent, by visual inspection, i.e., about 7–10 days, at which point an antimitotic such as cytosine arabinoside is added to the medium to prevent overgrowth of fibroblasts.

The culture medium in the exterior (neuronal) compartment is replaced with culture medium containing 5.0 $\mu$M $CoCl_2$. The culture medium is removed from the interior of the insert and replaced with culture medium containing the chemical to be tested. The level of medium in the interior of the insert should be below that of the exterior compartment. This prevents access of test compound to the neuronal cell bodies in the exterior compartment. After about 1–20 minutes, the inserts are removed and the neuronal cells are exposed to $(NH_4)_2S$ (0.12%, w/v, 5–20 minutes) solution. The resulting precipitate can be intensified following the silver intensification method of Nagy et al., supra. The number of stained versus unstained neurons in 5–20 fields of view is counted in treated inserts and compared with those numbers in the control inserts. Several wells can be tested simultaneously and in replicate with different concentrations of the chemical to determine the range of effective concentrations. Control wells are run which 1) do not receive the chemical-containing medium and 2) receive any necessary solvent controls.

EXAMPLE 6

The same cell culture procedure as in Example 5 is followed, with the following exception in the method for measuring neuronal activation. In this example, the neurons are loaded with FURA-2AM (2–10 $\mu$M, 30–60 minutes) by incubating the outer, outside surface of the insert in FURA-2AM-containing medium. Loading of cells in the inner chamber is prevented by maintaining the level of the interior medium several mm higher than that in the outer chamber. The inserts are placed on the stage of an inverted fluorescence microscope/imaging device with the neurons in a medium containing 2 $\mu$M $Ca^{2+}$. The insert is placed in a special well with a UV-transmitting glass bottom. The test chemical(s) are presented to the inner (epithelial cell) chamber. When test chemicals are added, the fluid level in the outer chamber is raised to be above that of the inner chamber. This prevents access of test compounds to the neuronal cell bodies. Intraneuronal calcium concentration is calculated from the ratio of fluorescence intensity values obtained from illumination at 340 to 360 nm. The response of neurons to the test chemical(s) is compared to that of control neurons from inserts that received control medium or solvent controls in the inner chamber.

EXAMPLE 7

The same procedures as in Example 2 or 6 are followed with the following modification. Instead of measuring neuronal activation with FURA-2 quantitation of intracellular $Ca^{2+}$, membrane potential is measured by loading the neurons with a voltage-sensitive fluorescent dye, such as Di-4-

ANEPPS. Montana, et al., *Biochemistry*, 28: 4536–4539, 1989, incorporated herein by reference. Ratiometric determination of membrane potential is performed similarly to Example 5 with the exception that different florescent excitation wavelengths are used depending upon which dye is used.

EXAMPLE 8

The same procedure as set forth in Example 5, 6 or 7 is followed with the exception that the hypersensitization as a result of exposure to more than one stimulus is tested. For example, the interior of the insert is directly exposed to U.V. radiation for a period of about 0–60 minutes. The test chemical is then added and the remainder of the procedure as set forth in any one of the aforementioned examples is followed. Controls are run in which no first conditioning stimulus is used, and in which no subsequent stimulus or test chemical is used.

What is claimed is:

1. A method for assessing the sensory irritation of chemicals in vitro comprising:
    a) cultivating neonatal neurons isolated from sensory ganglia in vitro in a culture medium containing nerve growth factor for a period of from about 2 to about 10 days;
    b) introducing $Ca^{++}$ or cobalt ions to said medium;
    c) adding a chemical to be tested to said culture medium and incubating for a period of up to about 1 hour;
    d) adding a means for measuring the uptake of $Ca^{++}$ or cobalt by said neurons; and
    e) comparing said uptake with that of a control culture of neurons to which the chemical has not been added.

2. The method of claim 1 wherein the $Ca^{++}$ or cobalt ions are introduced simultaneously with said chemical.

3. The method of claim 1 wherein the uptake of $Ca^{++}$ is measured using fluorescent staining.

4. A method for assessing the sensory irritation of chemicals on a particular target tissue in vitro comprising:
    a) cultivating neonatal neurons isolated from sensory ganglia in a first chamber and target tissue cells in a second chamber, said first and second chambers being on parallel planes and separated by a material permitting said neurons to innervate said target tissue cells, wherein said neurons and said target tissue cells are cultured in a culture medium containing nerve growth factor for a period of from about 2 to about 10 days;
    b) introducing $Ca^{++}$ or cobalt ions to medium in said first chamber;
    c) adding a chemical to be tested to said culture medium in said second chamber and incubating for a period of from about 1 minute to about 1 hour;
    d) adding a means for measuring the uptake of $Ca^{++}$ or cobalt by said neurons to said first chamber; and
    e) comparing said uptake with that of a control culture of neurons to which the chemical has not been added.

5. The method of claim 4 wherein said target tissue cells are selected from the group consisting of epithelial, endothelial, visceral organ, and muscle cells.

6. The method of claim 4 further comprising mast cells at a density representative of the density of said mast cells in said target tissue in vivo in said second chamber.

7. The method of claim 4 wherein the uptake of $Ca^{++}$ is measured using fluorescent microscopy.

8. A method for assessing the sensory irritation of chemicals on a particular target tissue in vitro comprising:
    a) cultivating neonatal neurons isolated from sensory ganglia in a first chamber and target tissue cells in a second chamber, said first and second chambers being on parallel planes separated by a material permitting said neurons to innervate said target tissue cells, wherein said neurons and said target tissue cells are cultured in a culture medium containing nerve growth factor for a period of from about 2 to about 10 days;
    b) adding a voltage-sensitive fluorescent dye to said first chamber;
    c) adding a chemical to be tested to said culture medium in said second chamber and incubating for a period of up to about 20 minutes; and
    d) measuring changes in membrane potential.

9. The method of claim 8 wherein said target tissue cells are selected from the group consisting of epithelial, endothelial, visceral organ and muscle cells.

10. The method of claim 8 further comprising mast cells at a density representative of the density of mast cells in said target tissue in vivo in said second chamber.

11. A method for assessing the sensory irritation of chemicals in vitro comprising:
    a) cultivating neonatal neurons isolated from sensory ganglion in vitro in a culture medium containing nerve growth factor for a period of from about 2 to about 10 days;
    b) adding a first stimulus to said neurons and incubating for a period of up to about 2 days;
    c) introducing $Ca^{++}$ or cobalt ions to said medium;
    d) adding a second stimulus to said neurons and incubating for a period of up to about 20 minutes;
    e) adding a means for measuring the uptake of $Ca^{++}$ or $Co^+$ by said neurons after said second stimulus has been added; and
    f) comparing said uptake with that of a control culture of neurons to which the first stimulus has not been added, a control culture to which the second stimulus has not been added, or a control culture to which neither stimulus has been added.

12. The method of claim 11 wherein the first stimulus is selected from the group consisting of thermal, photic, or chemical stimulus.

13. The method of claim 11 wherein the second stimulus is selected from the group consisting of thermal, photic, or chemical stimulus.

14. The method of claim 11 wherein said $Ca^{++}$ or cobalt ions are introduced prior to said second chemical.

15. A method for assessing the sensory irritation of chemicals on a particular target tissue in vitro comprising:
    a) cultivating neonatal neurons isolated from sensory ganglia in a first chamber and target tissue cells in a second chamber, said first and second chambers being on parallel planes separated by a material permitting said neurons to innervate said target tissue cells, wherein said neurons and said target tissue cells are cultivated in a culture medium containing nerve growth factor for a period of from 2 to about 10 days;
    b) adding a first stimulus to said target tissue cells in said second chamber and incubating for a period of up to about 2 days;
    c) introducing $Ca^{++}$ or cobalt ions to the medium in said first chamber;
    d) adding a second stimulus to said target tissue cells in said second chamber and incubating for a period of up to about 20 minutes;

e) adding a means for measuring the uptake of $Ca^{++}$ or cobalt ions by said neurons after said second stimulus has been added; and f) comparing said uptake with that of a control culture of neurons to which the first stimulus has not been added, a control culture to which the second stimulus has not been added, or a control culture to which neither stimulus has been added.

16. The method of claim 15 wherein the first stimulus is selected from the group consisting of thermal, photic, or chemical stimulus.

17. The method of claim 15 wherein the second stimulus is selected from the group consisting of thermal, photic, or chemical stimulus.

18. The method of claim 15 wherein said target tissue cells are selected from the group consisting of epithelial, endothelial, visceral organ and muscle cells.

19. The method of claim 15 further comprising mast cells at a density representative of the density of said mast cells in said target tissue in vivo in said second chamber.

20. The method of claim 15 wherein $Ca^{++}$ or cobalt ions are introduced simultaneously with said second stimulus.

21. The method of claim 15 wherein the uptake of $Ca^{++}$ is measured using fluorescent imaging technology.

22. An assay kit for assessing the sensory irritation of chemicals in vitro comprising:

a) a tissue culture medium containing nerve growth factor;

b) tissue culture plates;

c) inserts sized to fit in individual wells of said tissue culture plates;

d) a source of $Ca^{++}$ or cobalt ions; and e) a means for measuring the uptake of $Ca^{++}$ or cobalt ions by cells cultured in said medium.

23. The kit of claim 22 wherein said means for measuring the uptake of $Ca^{++}$ is a change in fluorescence intensity.

24. The kit of claim 22 wherein said means for measuring the uptake of $Ca^{++}$ is a change in membrane voltage by fluorescence intensity.

25. The kit of claim 22 further comprising neuronal cells.

26. The kit of claim 22 further comprising target tissue cells.

27. A co-culture system for testing the sensory irritation of chemicals in vitro comprising target tissue cells cultured in a plane separate from and parallel to neuronal cells, said target tissue cells being separated from said neuronal cells by a material permitting innervation by neurites of the neuronal cells into the target tissue cells, wherein said neurites are not directly exposed to chemicals applied only to the target tissue cells.

28. The system of claim 27 wherein said target tissue is selected from the group consisting of skin, respiratory, hepatic, gastrointestinal, nasal, corneal, and oral tissue.

29. The system of claim 27, further comprising mast cells at a density typical for said target tissue in vivo.

* * * * *

UNITED STATES PATENT AND TRADEMARK OFFICE
CERTIFICATE OF CORRECTION

PATENT NO. : 5,811,256
DATED : September 22, 1998
INVENTOR(S) : Bruce P. Bryant

It is certified that error appears in the above-identified patent and that said Letters Patent is hereby corrected as shown below:

Col. 3, line 36, please delete "epithelium" and insert therefor --target tissue--;

Col. 3, line 67, after "the invention." please insert
-- Cellular elements, Matrigel, tissue matrix and culture medium layers are not drawn to scale. The bottom of the culture insert is 12mm diameter.--

Col. 8, line 59, please delete "$\leqq$" and substitute therefor -- $\leq$ --.

Signed and Sealed this

Sixth Day of March, 2001

NICHOLAS P. GODICI

*Attest:*

*Attesting Officer*  *Acting Director of the United States Patent and Trademark Office*